United States Patent [19]

Arni et al.

[11] 4,105,688

[45] Aug. 8, 1978

[54] PROCESS FOR THE PRODUCTION OF MALONIC ACID DINITRILE AND PURIFICATION THEREOF

[75] Inventors: Urs Arni, Brig; Adriano Faucci; August Stocker, both of Visp, all of Switzerland

[73] Assignee: Lonza, Ltd., Valais, Switzerland

[21] Appl. No.: 137,592

[22] Filed: Apr. 26, 1971

Related U.S. Application Data

[62] Division of Ser. No. 822,724, May 7, 1969, Pat. No. 3,655,721.

[30] Foreign Application Priority Data

| May 9, 1968 [CH] | Switzerland | 6964/68 |
| Jun. 18, 1968 [CH] | Switzerland | 9059/68 |
| Jun. 24, 1968 [CH] | Switzerland | 9383/68 |

[51] Int. Cl.² ............... C07C 120/00; C07C 121/22; B01D 3/34
[52] U.S. Cl. .................. 260/465.8 R; 260/465 H; 203/38
[58] Field of Search ............. 260/465.8, 465.2, 465 H, 260/465.8 R; 203/38

[56] References Cited

U.S. PATENT DOCUMENTS

| 2,799,697 | 7/1957 | Maxion | 260/465.2 |
| 2,809,986 | 10/1957 | Flisik et al. | 260/465.2 |
| 3,206,500 | 9/1965 | Puls et al. | 260/465.9 |
| 3,322,814 | 5/1967 | Iapelli | 260/465.1 |
| 3,417,126 | 12/1968 | Taguchi et al. | 260/465.8 R |
| 3,541,133 | 11/1970 | Johnson et al. | 260/465.8 R |
| 3,616,269 | 10/1971 | Aelony et al. | 260/465.8 R X |

FOREIGN PATENT DOCUMENTS

44-2,453 1/1969 Japan ................... 260/465.8

OTHER PUBLICATIONS

Holmes; Organic Reactions; vol. 2; 1948, pp. 64, 65, 74, 75.

Primary Examiner—Joseph Paul Brust
Attorney, Agent, or Firm—Virgil H. Marsh

[57] ABSTRACT

Malonic acid dinitrile is prepared by reacting acetonitrile and cyanogen chloride in the gaseous phase at temperatures from 740° to 780° C. Temperatures from 750° to 760° C. with molar ratios of 1:1 to 1:5 of cyanogen chloride to acetonitrile are preferred. The crude mixture containing malonic acid dinitrile may be purified by conversion of the principal impurities to easily separable compounds by a Diels-Alder or selective hydrogenation reaction.

14 Claims, No Drawings

PROCESS FOR THE PRODUCTION OF MALONIC ACID DINITRILE AND PURIFICATION THEREOF

This application is a division of U.S. patent application Ser. No. 822,724, filed May 7, 1969, now U.S. Pat. No. 3,655,721.

BACKGROUND OF THE INVENTION

1. Field of the Invention

This invention relates to a process for the production of malonic acid dinitrile from acetonitrile and cyanogen chloride in the gaseous phase and purification thereof.

U.S. Pat. No. 2,553,406 discloses that malonic acid dinitrile can be obtained by reacting acetonitrile and cyanogen chloride for a period of from 5 to 15 seconds at a temperature above 600° C. and preferably at a temperature of from 650° to 700° C. According to the example, the yields amount to less than 18%. It is also stated in this patent that the yields are reduced even further by exceeding 700° C.

U.S. Pat. No. 2,606,917 explains that where high temperatures are used, the reaction is accompanied both by decomposition and by the separation of carbon and polymers. According to this patent, the disadvantages can be avoided by using an inert gas. Unfortunately, the use of an inert gas does not provide an improvement in the poor yield of malonic acid dinitrile. Example 7 teaches a yield of only 16.8% is obtained at a reaction temperature of 650° C. for a duration of 6 seconds with a cyanogen chloride to acetonitrile to carbon dioxide molar ratio of 1:3:7.2.

Japanese Patent Publication 16506/66 discloses the yields are improved by introducing a small quantity of chlorine as catalyst into the gaseous reaction components i.e. acetonitrile and cyanogen chloride. The yields are thereby improved to approximately 70%. However, the use of chlorine as a catalyst results in the formation of large quantities of fumaric acid dinitrile and maleic acid dinitrile as by-products. This is particularly disadvantageous because maleic acid dinitrile is extremely difficult to separate from malonic acid dinitrile. In addition, the use of chlorine causes a considerable expense for apparatus.

The malonic acid dinitrile reaction product of acetonitrile and cyanogen chloride contains as contaminating by-products fumaric acid dinitrile and maleic acid dinitrile. The removal of these by-products from the reaction mixture involves considerable difficulty because of similarities in the physical constants.

DESCRIPTION OF THE INVENTION

We have discovered that improved yields of malonic acid dinitrile are obtained by reacting acetonitrile and cyanogen chloride in the gaseous phase in the narrow temperature range of 740° to 780° C. Contrary to prior art teachings of reduced yields at reaction temperatures above 700° C. we obtain yields up to 70% without chlorine present in the gaseous reaction admixture at the above temperatures. Temperatures in the range of 750° to 760° C. are preferred.

Operating at temperatures higher than 780° or lower than 740° results in lower yields. The increased temperatures cause decomposition which further increases contamination. Ordinarily, the process according to the invention is conducted at a molar ratio of cyanogen chloride to acetonitrile of 1:1 to 1:5 and preferably of 1:3 to 1:4.

We have also discovered that by purification of the crude mixture using a Diels-Alder reaction or selective hydrogenation, malonic acid dinitrile having a purity in the order of 99% or higher can be obtained.

Pipe shaped reactors, such as quartz pipes or metal pipes, are suitable for conducting the instant process. The gaseous reactants can be fed to the reactor in a preheated state and the residence time of the reactants in the reactor is usually 1 to 15 seconds, and preferably at 8 to 11 seconds.

The reaction products are cooled immediately to temperatures of 20° to 50°, preferably 25° to 30° C. after they leave the reactor. Cooling brine is a very effective coolant. The malonic acid dinitrile is then isolated from the cooled mixture.

According to one embodiment of the present invention, the fumaric acid dinitrile and the maleic acid dinitrile contaminants are separated from the malonic acid dinitrile contained in the reaction mixture by converting through a Diels-Alder reaction into the corresponding Diels-Alder addition compounds which are more easily separated from malonic acid dinitrile.

Compounds with a conjugated double bond are used as reaction components for the Diels-Alder reaction and butadiene, isoprene, dimethylbutadiene, piperylene, anthracene, perylene, furan, sorbic acid are examples which are suitable. Preferably either butadiene or anthracene is used.

Depending on which Diels-Alder reaction components are used, the addition product will be either a solid or liquid at temperatures above the melting point of malonic acid dinitrile. If solid addition products are obtained, for example when anthracene or perylene are used, then the separation of the Diels-Alder reaction products can be conducted by simple filtration or centrifuging at temperatures above the melting point of the malonic acid dinitrile, e.g. at temperatures of 35° to 40° C. When liquid reaction products are obtained, for example when butadiene is used, then the separation can be conducted by simple distillation of the malonic acid dinitrile under vacuum.

The Diels-Alder reaction is conducted in the reaction mixture obtained from acetonitrile-cyanogen chloride reaction. Reaction temperatures of 40° to 150° C. are preferred and the reaction may be conducted in an autoclave if desired. However, it is advantageous to first remove any unreacted starting materials by distillation and separate other impurities present in small quantities such as, for example beta-chloropropionitrile by another distillation under vacuum at 5 to 30 mm Hg prior to the Diels-Alder reaction. This embodiment of the purification may be conducted continuously or batch by batch and the continuous reaction is effectively conducted in a tube-type reactor.

According to another embodiment of the present invention, the fumaric and maleic acid dinitriles contained in the reaction mixture are converted to succinic acid dinitrile by selective hydrogenation with the equivalent quantity of hydrogen in the presence of a hydrogenation catalyst. The malonic acid dinitrile is then easily separated by fractionated distillation.

The hydrogenation can be conducted in the reaction mixture as obtained from the reaction of acetonitrile and cyanogen chloride. However, the reaction mixture is preferably distilled under vacuum (for example at 80° to 110° C. and 11 mm Hg), to separate the unreacted materials. Furthermore, it is also advantageous to dissolve the reaction mixture in an inert solvent and then conduct the hydrogenation. Examples of inert solvents, which will remain stable during the hydrogenation conditions are lower alcohols, such as methanol, ethanol, propanol, butanol; saturated hydrocarbons, such as benzine; aromatic hydrocarbons, such as benzene; ethers, such as dimethyl ether, diethyl ether, tetrahydrofuran and acetonitrile. The quantity of solvent used is not critical and as an example, 300 to 700 g per 100 g of reaction mixture is suitable.

The selective hydrogenation can be conducted under normal pressure and at room temperature. Naturally, higher pressures can also be used up to about 80 atm., as can higher temperatures, up to about 100° C.

Hydrogenation catalysts are well known. Examples of suitable catalysts include Raney nickel, Raney cobalt, copper, copper catalysts, such as copper chromite and preferably, palladium black and platinum black.

After the hydrogenation, the solvent is distilled off and malonic acid dinitrile is separated from the residue by fractionated distillation. In order to avoid decomposition of the malonic acid dinitrile, the distillation should be conducted under vacuum, for example 0.5 to 15 mm Hg.

The ability to hydrogenate the double-bonded carbon so selectively that no attack on nitrile groups occurs in totally unexpected.

EXAMPLE I

A mixture of cyanogen chloride and acetonitrile having a mole ratio of 1:3.6 was introduced into a quartz tube heated to 760° C. The tube had a length of 1.4 m and an inside diameter of 40 mm. Over a period of 3 hours, 750 g of acetonitrile and 312 g of cyanogen chloride were reacted. The residence time of the reactants in the tube was 9.8 seconds. The reaction products were immediately cooled with brine and the mixture contained 230 g of malonic acid dinitrile which corresponded to a yield of 68.4% of theoretical.

EXAMPLE II

The Diels-Alder reaction was used to purify 100 g of the reaction product of Example I. The mixture contained 97 g malonic acid dinitrile, 2 g maleic acid dinitrile and 1 g fumaric acid dinitrile which was reacted with 7 g of anthracene in a glass reaction vessel with stirring for two hours at 140° C. After cooling to 35° C., the Diels-Alder addition compound was filtered off at this temperature. The filtrate was distilled at 12 mm Hg to produce 92 g of malonic acid dinitrile with a purity over 99%. The yield amounted to 95% of the malonic acid dinitrile in the crude mixture.

EXAMPLE III

A reaction product obtained by the reaction of acetonitrile and cyanogen chloride, according to the present invention had residual starting material (acetonitrile) removed by distillation. Subsequently, additional contaminates (especially beta-chloropropionitrile) were removed by vacuum (13 mm Hg) distillation. 80 g of this reaction mixture now contained 96% malonic acid dinitrile. The mixture was reacted in an autoclave with 4 g of butadiene and heated for 10 hours at 100°–110° C. After distillation at 13 mm Hg, 74.7 g of pure malonic acid dinitrile having a purity of 99.8% were obtained. This corresponds to a yield of 97%.

EXAMPLE IV 160 g of a mixture having a malonic acid dinitrile content of 92% and about 8% fumaric acid dinitrile-maleic acid dinitrile combined was dissolved in 800 cc methanol. Hydrogenation was accomplished in the presence of 1.6 g of palladium black at room temperature under atmospheric pressure. The quantity of hydrogen (4320 cc) required for the hydrogenation of the unsaturated nitriles was absorbed in about 5½ hours. After evaporation of the methanol, the remaining mixture was fractionated under vacuum in a short packed column. The main fraction (weight 124.3 g) overflowed at 11 mm Hg between 98°–99° C. and consisted of malonic acid dinitrile with a purity of 99.8%.

During the distillation, small quantities of ammonia developed. Therefore, the main fraction was distilled once more (short cut distillation) with the addition of very small quantity of sulfuric acid. The resulting malonic acid dinitrile was colorless and free of ammonia. Purity of the final product was 99.91%.

We claim:

1. A method for purifying malononitrile containing as contaminants similarly boiling dienophiles formed in the preparation thereof containing a mixture of maleic acid dinitrile and fumaric acid dinitrile which comprises contacting the impure malononitrile with a member selected from the group consisting of butadiene, isoprene, dimethylbutadiene, piperylene, anthracene, perylene, furan and sorbic acid to effect adduction of said dienophiles and thereupon distilling the adduction reaction mixture to recover an overhead malononitrile fraction having a substantially reduced content of said dienophiles.

2. A method in accordance with claim 1 wherein said impure molononitrile is in the crude form thereof resulting from the reaction of acetonitrile and cyanogen chloride.

3. A method in accordance with claim 2 wherein the adduction of said crude malononitrile is effected at ambient temperature.

4. A method in accordance with claim 1 wherein said impure malononitrile consists essentially of malononitrile and said dienophiles.

5. A method in accordance with claim 4 wherein said dienophiles consist essentially of a mixture of fumaronitrile and maleonitrile.

6. A method for purifying malonitrile containing as contaminants fumaronitrile and maleonitrile formed in the preparation thereof which comprises contacting the impure malononitrile with a Diels-Alder reactant to effect adduction of said fumaronitrile and maleonitrile and thereupon distilling the adduction reaction mixture to recover an overhead malononitrile fraction having a substantially reduced constant content of said fumaronitrile and maleonitrile.

7. A method in accordance with claim 6 wherein said impure malonitrile is in the crude form thereof resulting from the reaction of acetonitrile and cyanogen chloride.

8. A method in accordance with claim 7 wherein the adduction of said crude malononitrile is effected at ambient temperature.

9. A method in accordance with claim 6 wherein said impure malononitrile consists essentially in malononitrile and said dienophiles.

10. A method for purifying malononitrile containing as contaminants fumaronitrile and maleonitrile formed in the preparation thereof which comprises contacting the impure malonitrile with a Diels-Alder reactant having at least two conjugated double bonds to effect adduction of said fumaronitrile and maleonitrile and thereon separating malononitrile which has a substantially reduced content of said fumaronitrile and maleonitrile from the adduction reaction mixture.

11. A method in accordance with claim 10 wherein said impure malononitrile is in the crude form thereof resulting from the reaction of acetonitrile and cyanogen chloride.

12. A method in accordance with claim 11 wherein the adduction of said crude malonotrile is effected at ambient temperature.

13. The process for the production and purification of malonic acid dinitrile which comprises: (a) reacting a reaction admixture consisting of acetonitrile and cyanogen chloride in the gaseous phase at a temperature between 740° and 780° C., whereby an admixture of malonic acid dinitrile, maleic acid dinitrile and fumaric acid dinitrile results; (b) treating said resultant admixture which contains malonic acid dinitrile, maleic acid dinitrile and fumaric acid with a Diels-Alder reaction compound having at least two conjugated double bonds, which involves a Diels-Alder addition reaction, said maleic acid dinitrile and said fumaric acid dinitrile being converted into the corresponding Diels-Alder addition compounds; and (c) separating said addition compounds from said malonic acid dinitrile, whereby purified malonic acid dinitrile is obtained.

14. A process for the production and purification of malonic acid dinitrile which comprises: (a) reaction a reaction admixture consisting of acetonitrile and cyanogen chloride in the gaseous phase at a temperature between 740° and 780° C., whereby a product admixture of malonic acid dinitrile, maleic acid and fumaric acid dinitrile results; (b) treating said resultant product admixture which contains malonic acid dinitrile, maleic acid dinitrile and fumaric acid dinitrile with a Diels-Alder reactant which involves a Diels-Alder addition reaction purification procedure which converts said maleic acid dinitrile and said fumaric acid dinitrile being converted into the corresponding Diels-Alder addition compounds; and (c) separating said addition compounds from said malonic acid dinitrile, whereby purified malonic acid dinitrile results.

* * * * *